(12) United States Patent
Udaka et al.

(10) Patent No.: US 9,724,403 B2
(45) Date of Patent: *Aug. 8, 2017

(54) THERAPEUTIC AGENT FOR CANCER

(71) Applicants: NATIONAL UNIVERSITY CORPORATION KOCHI UNIVERSITY, Kochi (JP); NEC CORPORATION, Tokyo (JP)

(72) Inventors: Keiko Udaka, Kochi (JP); Masahide Ishibashi, Kagawa (JP)

(73) Assignees: NEC CORPORATION, Tokyo (JP); NATIONAL UNIVERSITY CORPORATION KOCHI UNIVERSITY, Kochi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/700,525

(22) Filed: Apr. 30, 2015

(65) Prior Publication Data

US 2015/0265693 A1 Sep. 24, 2015

Related U.S. Application Data

(62) Division of application No. 12/449,377, filed as application No. PCT/JP2008/052070 on Feb. 7, 2008, now Pat. No. 9,045,556.

(30) Foreign Application Priority Data

Feb. 7, 2007 (JP) ................................ 2007-028081

(51) Int. Cl.
  *A61K 39/02* (2006.01)
  *A61K 39/00* (2006.01)
  *C07K 14/47* (2006.01)

(52) U.S. Cl.
  CPC ........ *A61K 39/099* (2013.01); *A61K 39/0011* (2013.01); *C07K 14/4747* (2013.01); *C07K 14/4748* (2013.01); *A61K 2039/521* (2013.01); *A61K 2039/55505* (2013.01); *A61K 2039/55594* (2013.01)

(58) Field of Classification Search
  None
  See application file for complete search history.

(56) References Cited

U.S. PATENT DOCUMENTS

| 9,045,556 | B2 * | 6/2015 | Udaka | ............... | A61K 39/0011 |
| 2004/0126362 | A1 | 7/2004 | Gaiger et al. | | |
| 2005/0249756 | A1 | 11/2005 | Dalgleish et al. | | |

FOREIGN PATENT DOCUMENTS

| EP | 1 462 456 | 9/2004 |
| EP | 1 757 687 | 2/2007 |
| JP | 6-80574 | 3/1994 |
| JP | 10-503473 | 3/1998 |
| JP | 11-512076 | 10/1999 |
| JP | 2002-523471 | 7/2002 |
| JP | 2002-531520 | 9/2002 |
| WO | 98/11918 | 3/1998 |
| WO | 00/12125 | 3/2000 |
| WO | 00/33869 | 6/2000 |
| WO | 00/53219 | 9/2000 |
| WO | 2005/105993 | 11/2005 |

OTHER PUBLICATIONS

International Search Report issued Apr. 22, 2008 in International (PCT) Application No. PCT/JP2008/052070.
Y. Oka et al., "Cancer Immunotherapy Targeting Wilms' Tumor Gene WT1 Product", J. Immunol., vol. 164, pp. 1873-1880, 2000.
Y. Oka et al., "Induction of WT1 (Wilms's Tumor Gene)-Specific Cytotoxic T Lymphocytes by WT1 Peptide Vaccine and the Resultant Cancer Regression", Proc. Natl. Acad. Sci. U.S.A., vol. 101, No. 38, pp. 13885-13890, 2004.
S. A. Rosenberg et al., "Cancer Immunotherapy: Moving Beyond Current Vaccines", Nat. Med., vol. 10, No. 9, pp. 909-915, Sep. 2004.
S. Mosolits et al., "Therapeutic Vaccination in Patients with Gastrointestinal Malignancies. A Review of Immunological and Clinical Results", Annals of Oncology, vol. 16, pp. 847-862, 2005.
D. Nagorsen et al., "Clinical and Immunologic Responses to Active Specific Cancer Vaccines in Human Colorectal Cancer", Clin. Cancer Res., vol. 12, No. 10, pp. 3064-3069, May 15, 2006.
A. Nencioni et al., "Anticancer Vaccination Strategies", Annals of Oncology, vol. 15, Supplement 4, pp. 153-160, 2004.
P. Romero et al., "Monitoring Tumor Antigen Specific T-Cell Responses in Cancer Patients and Phase I Clinical Trials of Peptide-Based Vaccination", Cancer Immunol. Immunother., vol. 53, pp. 249-255, 2004.
R. E. M. Toes et al., "Peptide Vaccination Can Lead to Enhanced Tumor Growth Through Specific T-Cell Tolerance Induction", Proc. Natl. Acad. Sci., vol. 93, pp. 7855-7860, Jul. 1996.
C. L. Slingluff et al., "Clinical and Immunologic Results of a Randomized Phase II Trial of Vaccination Using Four Melanoma Peptides Either Administered in Granulocyte-Macrophage Colony-Stimulating Factor in Adjuvant or Pulsed on Dendritic Cells", Journal of Clinical Oncology, vol. 21, No. 21, pp. 4016-4026, Nov. 1, 2003.

(Continued)

*Primary Examiner* — Shanon A Foley
*Assistant Examiner* — Myron Hill
(74) *Attorney, Agent, or Firm* — Wenderoth, Lind & Ponack, L.L.P.

(57) ABSTRACT

The present invention provides an adjuvant for cancer antigen peptide vaccines and virus antigen peptides, containing a pertussis vaccine as a primary ingredient. The present invention also provides a therapeutic agent for a cancer or viral infectious disease, and a prophylactic agent for metastasis or recurrence of cancer or onset of virus-induced tumor, containing a cancer antigen peptide or virus antigen peptide and a pertussis vaccine. A pertussis vaccine that can be suitably used is a whole cell body pertussis vaccine. The agents of the present invention can be safely administered in a plurality of doses.

1 Claim, 11 Drawing Sheets

(56) References Cited

OTHER PUBLICATIONS

D. E. Speiser et al., "Rapid and Strong Human CD8+ T Cell Responses to Vaccination with Peptide, IFA, and CpG Oligodeoxynucleotide 7909", The Journal of Clinical investigation, vol. 115, No. 3, pp. 739-746, Mar. 2005.

L. Fong et al., "Altered Peptide Ligand Vaccination with Flt3 Ligand Expanded Dendritic Cells for Tumor Immunotherapy", Proc. Natl. Acad. Sci. U.S.A., vol. 98, No. 15, pp. 8809-8814, Jul. 17, 2001.

F. Fallarino et al., "Th1 and Th2 Cell Clones to a Poorly Immunogenic Tumor Antigen Initate CD8+ T Cell-Dependent Tumor Eradication In Vivo", The Journal of Immunology, vol. 165, pp. 5495-5501, 2000.

K. Dredge et al., "Adjuvants and the Promotion of Th1-Type Cytokines in Tumour Immunotherapy", Cancer Immunol. Immunother. vol. 51, pp. 521-531, 2002.

S. A. Rosenberg et al., "Immunologic and Therapeutic Evaluation of a Synthetic Peptide Vaccine for the Treatment of Patients with Metastatic Melanoma", Nat. Med., vol. 4, No. 3, pp. 321-327, Mar. 1998.

T. Di Pucchio et al., "Immunization of Stage IV Melanoma Patients with Melan-A/MART-1 and gp100 Peptides plus IFN-α Results in the Activation of Specific CD8+ T Cells and Monocyte/Dendritic Cell Precursors", Cancer Res., vol. 66, No. 9, pp. 4943-4951, May 1, 2006.

A. C. Peterson et al., "Immunization with Melan-A Peptide-Pulsed Peripheral Blood Mononuclear Cells Plus Recombinant Human Interleukin-12 Induces Clinical Activity and T-Cell Responses in Advanced Melanoma", Journal of Clinical Oncology, vol. 21, No. 12, pp. 2342-2348, Jun. 15, 2003.

H. Nakajima et al., "WT1 Peptide Vaccination Combined with BCG-CWS is More Efficient for Tumor Eradication than WT1 Peptide Vaccination Alone", Cancer Immunol. Immunother., vol. 53, pp. 617-624, 2004.

A. Haugan et al., "Bordetella pertussis can act as adjuvant as well as inhibitor of immune responses to non-replicating nasal vaccines", Vaccine, vol. 22, pp. 7-14, 2003.

Office Action issued in corresponding Indonesian Patent Application No. W00200902169 issued Jul. 26, 2011 with partial English translation.

F. Kolbinger et al., "Humanization of a Mouse Anti-Human IgE Antibody: A Potential Therapeutic for IgE-Mediated Allergies", Protein Engineering, vol. 6, No. 8, pp. 971-980, 1993.

Office Action in corresponding Japanese Patent Application No. 2008-557158 issued on Sep. 20, 2012 with partial English translation.

C. M. Ausiello et al., "Cell-Mediated Immune Response of Healthy Adults to *Bordetella pertussis* Vaccine Antigens", The Journal of Infectious Diseases, vol. 178, No. 2, pp. 466-470, Mar. 1998.

H. Minagawa et al., "Endogenous Tumor Necrosis Factor Induction with *Bordetella pertussis* Vaccine as a Triggering Agent and its Therapeutic Effect on MM46 Carcinoma-Bearing Mice", Japan J. Cancer Res., vol. 79, No. 3, pp. 384-389, Mar. 1988.

M. Onishi et al. "Immunological Properties of Low Toxic Antitumor Lipopolysaccharide from *Bordetella pertussis*", Japanese Society of Immunology, vol. 21, p. 456, I-49, 1991 (in Japanese).

McNeil, C., J. National Cancer Institute, 2006, vol. 98, No. 5, pp. 301-302.

Liao, JP, Journal of Biology and Medicine, 2006, vol. 79, pp. 115-122.

Prikazsky et al., Int. J. Clin Pract. 2001, vol. 55, pp. 156-161.

Yano, et al., Microbiol. Immunol., 2007, vol. 51, pp. 685-699, abstract only used.

Supplementary European Search Report dated Apr. 18, 2011 in EP Application No. 08 71 0949.

T. Maruta et al., "Use of Alum and Inactive *Bordetella pertussis* for Generation of Antibodies Against Synthetic Peptides in Mice", Immunological Investigations, vol. 35, No. 2, pp. 137-148, Jan. 1, 2006.

Y. Oka et al., "Development of WT1 Peptide Cancer Vaccine Against Hematopoietic Malignancies and Solid Cancers", Current Medicinal Chemistry, vol. 13, pp. 2345-2352, Jan. 1, 2006.

A. Tsuboi et al., "WT1 Peptide-Based Immunotherapy for Patients with Lung Cancer: Report of Two Cases", Microbiology and Immunology, vol. 48, No. 3, pp. 175-184, Jan. 1, 2004.

Morita et al., "A Phase I/II Trial of a WT1 (Wilms' Tumor Gene) Peptide Vaccine in Patients with Solid Malignancy: Safety Assessment Based on the Phase I Data", Japanese Journal of Clinical Oncology, vol. 36, No. 4, pp. 231-236, Apr. 1, 2006.

J. Pinilla-Ibarz et al., "Improved Human T-Cell Responses Against Synthetic HLA-0201 Analog Peptides Derived from the WT1 Oncoprotein", Leukemia, vol. 20, pp. 2025-2033, Jan. 1, 2006.

J. Athanassiades et al., "Adjuvant Effect of *Bordetella pertussis* Vaccine to Sheep Erythrocytes in Mice: Enhancement of Cell-Mediated Immunity by Subcutaneous Administration of Adjuvant and Antigen", Infection and Immunity, vol. 18, No. 2, pp. 416-423, Nov. 1977.

T. L. M. Ten Hagen et al., "Role of Adjuvants in the Modulation of Antibody Isotype, Specificity, and Induction of Protection by Whole Blood-Stage *Plasmodium yoelii* Vaccines", The Journal of Immunology, vol. 151, No. 12, pp. 7077-7085, Dec. 15, 1993.

European Patent Office Communication under Rule 71(3) EPC dated Mar. 16, 2016 issued in corresponding European Patent Application No. 08710949.2.

M. Ryan et al., "Distinct T-cell subtypes induced with whole cell and acellular pertussis vaccines in children", Immunology, vol. 93, 1998, pp. 1-10.

* cited by examiner

SEQUENCE LISTING

<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Ser Ile Ile Asn Phe Glu Lys Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Arg Met Phe Pro Asn Ala Pro Tyr Leu
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Ile Ser Gln Ala Val His Ala Ala His Ala Glu Ile Asn Glu Ala Gly
1               5                   10                  15

Arg

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Ala Leu Leu Pro Ala Val Pro Ser Leu
1               5

THERAPEUTIC AGENT FOR CANCER

TECHNICAL FIELD

The present invention relates to a vaccine that helps treat cancers and viral infectious diseases and prevent metastases and recurrences of cancers and onset of virus-induced tumors, and to an adjuvant for production thereof.

BACKGROUND ART

A peptide immunotherapy for tumors using HLA class I-binding peptides has been performed for trial purposes. However, judging from the results of peptide immunotherapies obtained to date, administration of a tumor antigen peptide alone is not expected to be so effective (as far as past reports of treatment are concerned, there were almost no cases wherein the ratio of SD in RECIST ratings exceeded 10%) (non-patent references 1, 3).

Hence, to stimulate cytotoxic T lymphocytes (CTLs), a method is widely used wherein a peptide emulsified with Freund's incomplete adjuvant (FIA) is administered (non-patent references 1-3). A peptide suspended in FIA, as is evident from an increase in MHC tetramer-positive CD8 T cells or IFN-γ-secreting cells, allows peptide-specific T cells to proliferate. However, the CD8 T cells that have proliferated are unlikely to be completely activated as an effector; their therapeutic effect has been limited (non-patent references 4-6). In some cases, the peptide suspended in FIA can even cause antigen-specific immunological tolerance (non-patent reference 7). There is another problem of deteriorating the patient's QOL considerably because the FIA long persists under the skin, and also because papules persist for about 2 years and skin induration progresses as the number of administrations increases, although flare dissipates in 1 to 2 months.

In an attempt to increase peptide immunogenicity, many adjuvants have been tested in clinical studies. The purpose of use of these adjuvants is to provide CTLs with an anti-inflammatory environment by activating antigen-presenting cells (APCs) and/or helper T cells (Th). Dendritic cells are used as antigen-presenting cells for peptide pulsation to induce better tumor control (non-patent references 3, 8). Non-methylated deoxy-CpG, Toll-like receptor ligands (non-patent reference 9) and ligands that activate APCs, such as Flt3 (non-patent reference 10), have been introduced. Regarding helper activity, type Th1 responses induce optimal cellular immunity (non-patent references 11, 12). Recombinant cytokines secreted by Th cells and other immunopotentiating cells are used in clinical studies. These cytokines include IL-2 (non-patent reference 13), GM-CSF (non-patent reference 8), IFN-α (non-patent reference 14) and IL-12 (non-patent reference 15). Because commercial products of GMP (Good Manufacturing Practice) grade are available, the cytokines allow easy conduct of test treatment. However, these are no more than capable of replacing some of immune responses, and mainly stimulating either APCs or Th cells only. Additionally, the biological half-lives of cytokines are limited.

For the purpose of activating both APCs and Th cells under more natural conditions, use of the tubercle *bacillus* cell wall skeleton (BCG-CWS) has been developed (non-patent reference 16). However, BCG-CWS potently activates cellular immunity, so that the onset of open ulcer is unavoidable. For this reason, BCG-CWS cannot be used in patients with decreased immunity, like leukemia patients. BCG-CWS is also difficult to use in repeated immunization. Because peptides are apt to undergo decomposition by proteases in the serum, and disappear within several days, except for those bound to MHC molecules on the cell surface, frequent immunization is necessary. T cells, which essentially respond to a tumor autoantigen protein being a subject of immunological tolerance, are likely to lose activity; the cytotoxic activity thereof weakens unless administered once weekly. Therefore, being difficult to administer repeatedly, BCG-CWS is seriously faulty as an adjuvant for tumor immunotherapy.

non-patent reference 1: Rosenberg, S. A. et al., Nat. Med., vol. 10, p. 909-915 (2004)
non-patent reference 2: Oka, Y. et al., Proc. Natl. Acad. Sci. USA, vol. 101, p. 13885-13890 (2004)
non-patent reference 3: Mosolits, S. et al., Ann. Oncol., vol. 16, p. 847-862 (2005)
non-patent reference 4: Nagorsen, D. et al., Clin. Cancer Res., vol. 12, p. 3064-3069 (2006)
non-patent reference 5: Nencioni, A. et al., Ann. Oncol., vol. 15, p. 153-160 (2004)
non-patent reference 6: Romero, P. et al., Cancer Immunol. Immunother., vol. 53, p. 249-255 (2004)
non-patent reference 7: Toes, R. E. M. et al., Proc. Natl. Acad. Sci. USA, vol. 93, p. 7855-7860 (1996)
non-patent reference 8: Slingluff, C. L. et al., J. Clin. Oncol., vol. 21, p. 4016-4026 (2006)
non-patent reference 9: Speiser, D. E. et al., J. Clin. Invest., vol. 115, p. 739-746 (2005)
non-patent reference 10: Fong, L. et al., Proc. Natl. Acad. Sci. USA, vol. 98, p. 8809-8814 (2001)
non-patent reference 11: Fallarino, F. et al., J Immunol, vol. 165, p. 5495-5501 (2000)
non-patent reference 12: Dredge, K. et al., Cancer Immunol. Immunother., vol. 51, p. 521-531 (2002)
non-patent reference 13: Rosenberg, S. et al., Nat. Med., vol. 4, p. 321-327 (1998)
non-patent reference 14: Di Pucchio, T. et al., Cancer Res., vol. 66, p. 4943-4950 (2006)
non-patent reference 15: Peterson, A. et al., J. Clin. Oncology, vol. 21, p. 2342-2348 (2006)
non-patent reference 16: Nakajima, H. et al., Cancer Immunol. Immunother., vol. 53, p. 617-624 (2004)

DISCLOSURE OF THE INVENTION

Problems to be Solved by the Invention

It is an object of the present invention to provide an adjuvant for a cancer antigen or virus antigen peptide vaccine, wherein the adjuvant is effective in tumor-specific immunotherapy or immunotherapy for viral infectious disease, and hence to provide a therapeutic agent for cancer or viral infectious disease that is effective in the immunotherapy.

Means of Solving the Problems

The present inventors extensively investigated in view of the above-described problems, and found that a whole cell pertussis vaccine activates both antigen presenting cells (APCs) and helper T cells (Th), and that a vaccine comprising a cancer antigen or virus antigen peptide and a whole cell pertussis vaccine as an adjuvant exhibits excellent anti-tumor activity or anti-virus activity. Furthermore, the present inventors confirmed that the pertussis vaccine, unlike BCG-CWS, can be repeatedly administered at one-week intervals because the vaccine does not need emulsification before use as does FIA, and hardly produces flare and swelling, and have developed the present invention.

Accordingly, the present invention provides the following:

[1] A therapeutic agent for cancers or a prophylactic agent for cancer metastasis or recurrence, comprising a cancer antigen peptide and a pertussis vaccine,

[2] the agent of [1] above, wherein the pertussis vaccine is an adjuvant,

[3] the agent of [1] or [2] above, wherein the pertussis vaccine is a whole cell pertussis vaccine,

[4] the agent of any one of [1] to [3] above, wherein the cancer antigen peptide is a protein selected from the group consisting of WT1, survivin and prostate-specific antigen, or a peptide comprising a portion of the amino acid sequence thereof,

[5] the agent of any one of [1] to [4] above, wherein the cancer is a malignant tumor that highly expresses a protein selected from the group consisting of WT1, survivin and prostate-specific antigen,

[6] the agent of any one of [1] to [5] above, wherein the agent permits at least 3 times of immunizing inoculation,

[7] a therapeutic agent for viral infectious disease comprising a peptide derived from a virus that causes viral infectious disease and a pertussis vaccine,

[8] the agent of [7] above, wherein the pertussis vaccine is an adjuvant,

[9] the agent of [7] or [8] above, wherein the pertussis vaccine is a whole cell pertussis vaccine,

[10] the agent according to any one of [7] to [9] above, wherein the virus is a malignant tumor-inducing virus,

[11] the agent of [10] above, wherein the agent is to be used for prevention/treatment of a virus-induced malignant tumor,

[12] the agent of any one of [7] to [9] above, wherein the virus is selected from the group consisting of hepatitis C virus, influenza virus and dengue virus,

[13] the agent of any one of [7] to [12] above, wherein the agent permits at least 3 times of immunizing inoculation,

[14] an adjuvant for vaccine comprising a pertussis vaccine as a primary ingredient, and a cancer antigen peptide or virus peptide as an active ingredient,

[15] the adjuvant of [14] above, wherein the pertussis vaccine is a whole cell pertussis vaccine,

[16] the adjuvant of [14] or [15] above, wherein the virus is a malignant tumor-inducing virus,

[17] the adjuvant of [14] or [15] above, wherein the peptide is a protein selected from the group consisting of WT1, survivin and prostate-specific antigen, or a peptide comprising a portion of the amino acid sequence thereof, and

[18] the adjuvant of [14] or [15] above, wherein the virus is selected from the group consisting of hepatitis C virus, influenza virus and dengue virus.

Effect of the Invention

The therapeutic agent for cancer or viral infectious disease and prophylactic agent for metastases or recurrences of cancers or onset of virus-induced malignant tumors of the present invention comprise a cancer antigen or viral peptide and a pertussis vaccine. Pertussis vaccines exhibit excellent adjuvant activity in administration of cancer antigen peptides and viral peptides. Pertussis vaccines are widely used as vaccines as they are, and vaccines of GMP grade are available. Therefore, provided by the present invention is an effective and safe therapeutic agent for cancers and viral infectious diseases.

BEST MODE FOR CARRYING OUT THE INVENTION

Figure 1:
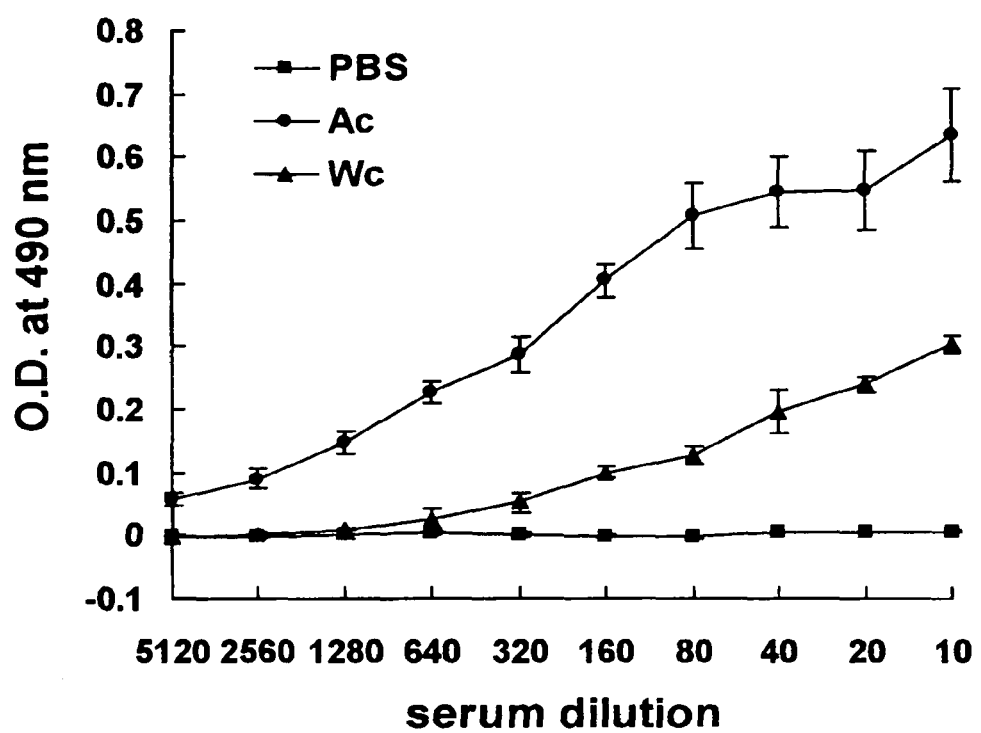
FIG. 1 A graphic representation of the helper-inducing activities of pertussis vaccines in the production of IgG antibodies against pertussis toxin and fibrous hemagglutinin. B6 mice were subcutaneously immunized with the PBS or the Ac or We pertussis vaccine once weekly. IgG antibody activities against pertussis toxin and fibrous hemagglutinin in the serum were determined by ELISA using a γ chain-specific secondary antibody. Here are shown antibody activities at one week after the 3rd immunization. The data are shown as mean and SD for two mice.

The present invention provides a therapeutic agent for cancers (or viral infectious diseases) and a prophylactic agent for metastases and recurrences of cancers (or onset of virus-induced malignant tumors), the agent comprising a cancer antigen peptide (or a peptide derived from a virus that causes a viral infectious disease) and a pertussis vaccine (hereinafter also referred to as "an agent of the present invention"). As mentioned herein, "treatment" is understood to include "mitigation of a symptom" and "progression suppression".

In the present invention, "a cancer antigen peptide" refers to a protein (peptide) having an activity to induce an immune reaction such as antibody production or cellular immunity; in particular, a protein (peptide) having a T cell inducing activity to stimulate cytotoxic T lymphocytes (CTLs) is particularly preferable. The cancer antigen peptide is not particularly limited, as far as it is a protein (peptide) having a T cell inducing activity; for example, HER-2/neu, MART-1, NY-ESO-1, Gp-100, MUC-1, p53, prostate-specific antigen (PSA), hTERT, WT1, survivin, CEA, MAGE and the like can be mentioned; the cancer antigen peptide is preferably WT1, survivin, PSA or the like, more preferably WT1. Specifically, as the WT1 antigen peptide, those described in WO 00/06602, WO 00/26249, WO 2006/030770 and the like can preferably be used. As the survivin antigen peptide, those described in WO 2006/080142 and the like can preferably be used.

Meanwhile, in the present invention, "a viral peptide" refers to a protein derived from a virus that causes some disease or condition by infecting to a mammal, including a human, or a peptide comprising a portion of the amino acid sequence thereof; examples include, but are not limited to, hepatitis C virus, hepatitis B virus, influenza virus, dengue virus, adult T cell virus, human immunodeficiency virus, papilloma virus and the like. In a preferred embodiment, the viral peptide is an antigen peptide derived from a tumor-related (tumorigenic) virus. Here, "a tumor-related peptide" refers to a protein derived from a group of viruses strongly associated with the onset of malignant tumors, including hepatitis C virus, or a peptide comprising a portion of the amino acid sequence thereof. Specifically, as the hepatitis C virus peptide, those described in WO 2005/105993 and the like can preferably be used.

As far as immunogenicity for an antigen is possessed, the cancer antigen peptide may be a cancer antigen or virus antigen peptide fragment.

A cancer antigen peptide can be prepared by, for example, a method described by Sambrook et al. (1989 Molecular cloning: a laboratory manual. $2^{nd}$ Ed. Cold Spring Harbor Lab., Cold Spring Harbor, N.Y.). Specifically, a cancer antigen peptide can be produced by, for example, culturing a transformant incorporating an expression vector comprising a nucleic acid that encodes a cancer antigen protein (peptide) to produce the cancer antigen protein (peptide), and separating and purifying the cancer antigen protein (peptide) from the culture obtained. A cancer antigen protein (peptide) can also be produced by a publicly known method of peptide synthesis. The method of peptide synthesis may be, for example, a method of solid phase synthesis or a method of liquid phase synthesis.

As "pertussis vaccines", a whole cell pertussis vaccine comprising a cell wall fraction of formaldehyde-treated or thermally inactivated *Bordetella pertussis*, a cell-free pertussis vaccine comprising a component semi-purified or purified from *Bordetella pertussis* (e.g., pertussis toxin, fibrous hemagglutinin and the like) and the like can be mentioned. Preferably, the pertussis vaccine is a whole cell pertussis vaccine, but depending on the subject patient and condition, a cell-free pertussis vaccine is sometimes useful.

Regarding how to prepare a pertussis vaccine, a publicly known method can be used without limitations. Commercial products of pertussis vaccines may be used, which are available from, for example, Bio Farma (Indonesia) and the like.

The ratio of cancer antigen peptide (or viral peptide) and pertussis vaccine contained in an agent of the present invention varies depending on the choice of antigen and the characteristics of pertussis vaccine, and cannot be generalized; for example, when both a WT1 antigen and a whole cell pertussis vaccine are used, 0.1 to 5 mg of peptide: $1\times10^8$ to $1\times10^9$ cells of whole cell pertussis vaccine can be mentioned as an example ratio in a single dose for an adult, and the ratio is preferably 0.5 to 4 mg of peptide: 1 to $7\times10^8$ cells of whole cell pertussis vaccine.

An agent of the present invention may further comprise a pharmaceutically acceptable carrier. As the pharmaceutically acceptable carrier, any carrier in common use for vaccine production can be used without limitations; specifically, saline, buffered saline, dextrose, water, glycerol, isotonic aqueous buffer solutions and combinations thereof can be mentioned. The carrier is preferably a sterilized one. This is formulated as appropriate with an emulsifier, a preservative (e.g., thimerosal), an isotonizing agent, a pH regulator, a deactivator (e.g., formalin) and the like.

The subject of administration of an agent of the present invention is not particularly limited, as far as it is an animal suffering from a cancer that highly expresses the protein from which the active ingredient cancer antigen peptide is derived, or infected with the virus from which the viral peptide is derived; for example, mammals, including humans, birds and the like can be mentioned.

An agent of the present invention preferably has a form suitable for the mode of administration of the vaccine; for example, injectable forms include solutions, suspensions or emulsions. Alternatively, as a form that can be treated to obtain a liquid solution, suspension or emulsion, a solid form such as a lyophilized preparation can be mentioned.

An agent of the present invention can be produced by a conventional method with the aforementioned cancer antigen peptide or viral peptide as an active ingredient, and a pertussis vaccine as an adjuvant ingredient, together with the aforementioned carrier. The cancer antigen peptide or viral peptide and pertussis vaccine may be contained in the agent at 0.1 to 5 mg of peptide and $1\times10^8$ to $1\times10^9$ cells of whole cell pertussis vaccine, preferably 0.5 to 4 mg of peptide and 1 to $7\times10^8$ cells of whole cell pertussis vaccine, for a single dose for an adult.

As a preferred preparation example, a method can be mentioned wherein a single dose of the peptide (for example, 3 mg) is dissolved in 300 μl of a solvent (e.g., 5% glucose solution), and this is admixed, just before administration, with $5\times10^8$ cells of whole cell pertussis vaccine suspended in 100 μl of a suspending agent (e.g., physiological saline) to obtain a total of 400 μl of a vaccine solution, but this is not to be construed as limiting.

The route for administration of an agent of the present invention is not particularly limited, but is preferably a topical administration. For example, intramuscular, subcutaneous, intradermal, intraperitoneal and other routes of administration can be mentioned; as methods of administration, injection and the like can be mentioned. Dermal, intranasal, and intraoral administration are also possible; as methods of administration, spraying, coating and the like can be mentioned.

The amount administered is determined in view of the subject's age, sex, body weight, drug tolerability and the like; usually, for a single dose for an adult, 0.1 to 5 mg of peptide and $1\times10^8$ to $1\times10^9$ cells of whole cell pertussis vaccine, preferably 0.5 to 4 mg of peptide and 1 to $7\times10^8$ cells of whole cell pertussis vaccine, can be administered once, twice or more. Preferably, multiple doses are administered; in this case, it is desirable that an agent of the present invention be administered at intervals of 1 to 4 weeks, preferably 1 to 2 weeks, more preferably 1 week, 3 times or more, preferably 6 times or more, more preferably 10 times or more, and still more preferably 12 times or more. In multiple-dose administration, the single dose of the peptide and/or pertussis vaccine may be changed as appropriate within the range mentioned above. Usually, a dosing protocol is often adopted wherein a low dose is first tested several times for the sake of safety test, and after safety is verified, the dose is increased. Before concomitant use with a pertussis vaccine, a safety test with the peptide administered alone may be performed. Furthermore, if an adverse reaction such as flare is observed after administration of the pertussis vaccine, it is desirable that the subject be followed up for the time being with the dosing protocol switched to transient administration of the peptide alone, or with a washout.

In the administration, it is important that the agent be administered in a way such that the peptide can arrive at as many lymph nodes as possible, as far as the burden on the patient is low. Because the number of peptides per cell bound onto the MHC molecule of antigen-presenting cells such as dendritic cells and the total number of dendritic cells that present the peptide and migrate to lymph nodes are important, it is more efficient to change sites to allow the peptide to reach some lymph nodes, rather than to administer the agent in a large amount to one site. However, because it has been empirically conjectured that if performed under conditions such that the same antigen is present at a high density in a portion of a wide surface area, immunization may be likely to induce type I allergies (immediate allergies: urticaria, anaphylactic shock, asthma and the like), usually, the agent is often administered to the skin at 1 to 2 sites close to each of the lymph nodes at the bases of the four limbs, totaling 4 to 8 sites.

Examples of preferred modes of administration include, but are not limited to, a method wherein to the skin at a total of 4 sites close to the lymph nodes in both axillae and both inguinal regions, at 100 μl per site by intradermal injection, and the like can be mentioned; as far as the above-described object can be accomplished, any modification is possible. For example, for a head and neck tumor patient, the agent may be administered at, instead of the inguinal regions, 2 sites on the left and right sides at the base of the neck (for the purpose of delivering an antigen to subclavian lymph nodes), and 1 site close to each axilla, totaling 4 sites. Regarding intradermal injection, a shot exceeding 100 μl at one site could be slightly painful and possibly cause a backflow and spill from the needle hole after injection; therefore, it is preferable that the dosing volume for one site be 100 μl or less.

Pertussis vaccines are characterized by lower prevalence of adverse reactions due to administration, such as flare, swelling, ulcers, and induration, than adjuvants in publicly known conventional peptide immunotherapies (about 5-20 mm erythemas are produced, which, however, almost disappears in about 48 hours). In particular, ulcers are feared to cause a fatal outcome in cancer patients, so this feature makes the present invention advantageously effective. Because an agent of the present invention does not need emulsification before use as does FIA, its administration does not produce persistent flare or papules. Furthermore, because the agent does not produce ulcers, which always develop with the use of BCG-CWS, once-a-week multiple-dose administration is possible, so that the risk of symptom exacerbation due to washouts can be minimized.

In a particularly preferred embodiment, an agent of the present invention comprises a peptide derived from the WT1 protein as a cancer antigen peptide. The WT1 protein is highly expressed in about 70% of spontaneously developing malignant tumors, and is particularly useful in the treatment of patients who express high levels of tumor antigens of malignant solid tumors such as renal cancer, lung cancer, esophageal cancer and other digestive cancers, ovarian cancer, breast cancer, brain tumor, and sarcomas, and leukemia and other malignant tumors of the blood. In another preferred embodiment, an agent of the present invention comprises an antigen peptide derived from hepatitis C virus as a viral peptide, and is useful in the treatment of hepatitis C and prevention of hepatitis C virus-induced malignant tumors (liver cancer and the like).

The present invention also provides a kit consisting of 1 or 2 or more containers containing 1 or 2 or more ingredients of an agent of the present invention.

Using an agent and kit of the present invention, it is possible to treat a cancer or viral infectious disease or to mitigate symptoms thereof. Therefore, the present invention provides a therapeutic method for a cancer or viral infectious disease, comprising administering an effective immunologically sensitizing amount of an agent of the present invention to a subject.

The present invention is hereinafter described in detail with reference to the following Examples, to which examples, however, the present invention is never limited.

EXAMPLES

Materials and Methods

Cells and Antibody

E.G7-OVA, an ovalbumin-transfected EL4 cell line (Moore, M. W. et al., (1988), Cell 54: 777-785), was kindly supplied by Dr. Michael Bevan through Dr. Herman N. Eisen. FBL3, an erythroleukemia line ($H-2^b$), was provided by Dr. Masaaki Miyazawa with permission through the courtesy of Dr. Bruce Chesebro.

Mice

OT1 transgenic mice (OT-1 tg) express a pair of TCRs specific for the ovalbumin peptide 257-264, which binds to the $H-2 K^b$ molecule, (Hogquist, K. A. et al., (1994), Cell 76: 17-27); this was kindly supplied by Dr. F. Carbone. The OT1 tg was mated with EGFP transgenic mice kindly provided by Dr. M. Okabe (Okabe, M. et al, (1997), FEBS Letters 407: 313-319). The two transgenic mouse lines were repeatedly backcrossed with the C57BL/6 (B6) background. The B6 mice were purchased from SLC (Shizuoka, Japan), and propagated in the SPF facility of the Kochi University School of Medicine. DO11.10 transgenic mice kindly supplied by Dr. D. Y. Loh were mated with BALB/c, and maintained as a homozygote with respect to a transgene that encodes a pair of TCRs specific for an OVA-II peptide that binds to $I-A^d$ (ovalbumin 323-339) (Murphy, K. M. et al., (1990), Science 250: 1720-1723).

Peptides

The OVA-I (SIINFEKL (SEQ ID NO:1)) peptide and the Db126 (RMFPNAPYL (SEQ ID NO:2)) peptide were manually synthesized by the Fmoc method. Each peptide was purified to a purity of >95% by reversed-phase HPLC, the molecular weight thereof being determined using a MALDI TOF mass analyzer (Voyager DE-RP, Applied Biosystems, Foster city, CA). Peptide concentrations were determined using the MicroBCA assay (Pierce, Rockford Ill.).

Adjuvants

The pertussis vaccine was produced from *Bordetella Pertussis* Tohama phase I strain bacterial cells, and supplied by the Research Foundation for Microbial Diseases of Osaka University (Bikenkai, Kannonji, Japan). The cell-free vaccine consisted of inactivated pertussis toxin and fibrous hemagglutinin, and mixed with aluminum phosphate. The whole cell vaccine comprised inactivated bacterial cells suspended in PBS.

IgG-Antibody Production in Mice Immunized with Ac or Wc Pertussis Vaccine

B6 mice were subcutaneously immunized with 5 μg of the cell-free (Ac) vaccine adsorbed to aluminum phosphate, or $2 \times 10^9$ cells of inactivated whole cell (Wc), each emulsified in Freund's incomplete adjuvant (FIA). One week after the 1st, 2nd and 3rd once-a-week immunization, the mice were killed, and sera were collected for ELISA analysis.

ELISA

A flat-based 96-well plate (SUMILON, Akita, Japan) was coated with the Ac vaccine at a concentration of 20 μg/ml, without aluminum salt, and blocked with 5% skimmed milk in PBS. Each mouse serum was serially diluted from a 1/10 dilution rate, and incubated at 4° C. for 1 hour. With an HRP-labeled goat anti-mouse IgG (γ chain-specific) antibody (Zymed, South San Francisco, Calif.) used as a secondary reagent, the serum was incubated at 4° C. for 30 minutes. An OPD substrate was added, and absorbance was measured at 490 nm.

In Vivo CTL Proliferation Experiment 10,000,000 splenocytes derived from the OT1tg were intravenously injected. The following day, each mouse was immunized with 50 nmoles of the OVA-I peptide in the back skin. The pertussis vaccine added as an adjuvant was 10 μg/mouse of the Ac vaccine adsorbed to aluminum phosphate, or $2 \times 10^7$ cells of the inactivated whole bacterial cell body. In the following week, the mice were booster-immunized with the same antigen. One week after the 2nd immunization, the mice were killed, and splenocytes were analyzed by flow cytometry. To identify transgenic TCRs, MR9-4, a phycoerythrin (PE)-labeled monoclonal anti-Vβ5-specific antibody (Kanagawa, O. et al., (1991), J. Immunol. 147: 1307-1314) was used.

Immunization with MHC Class I-Binding Peptide for Cytotoxicity Assay

B6 mice were immunized, with or without adjuvant, with 50 nmoles of the OVA-I peptide or 100 nmoles of the Db126 peptide (Udaka, K. et al, (2000), J Immunol 164: 1873-1880), dissolved in PBS, with the addition of 5 μg of the cell-free vaccine or $1 \times 10^7$ inactivated bacterial cells derived from the whole cell vaccine. The immunogen was intradermally injected into two sites in the back skin. Once-a-week peptide immunization was repeated 4 times.

Cytotoxicity Assay

Once-a-week immunization was performed 4 times in B6 mice as described above. One week after the final immunization, splenocytes were stimulated with EG7 cells in vitro. Briefly, splenocytes derived from one spleen were suspended in 10% FCS DMEM containing 5% rat Con A supernatant (32 ml). The EG7 cells were irradiated with 60 Gy from a $^{137}$Cs source, and added to the splenocytes at a density of $1 \times 10^5$ cells/ml. On day 5 after the stimulation, at various E/T ratios, cytolytic activity was measured by $^{51}$Cr release assay for 5 hours on 10,000 EG7 cells. %-specific lysis is the product of (experimental release−spontaneous release)/(total release−spontaneous release)×100.

Cytokine Analysis

Th1/Th2 cytokine secretion was measured using the Luminex 100 (Luminex Corporation, Austin, Tex.) and Fluorokine MAP mouse kit (R&D Systems Inc., Minneapolis, Minn.). DO11.10 mice were intradermally injected with 100 nmoles per mouse of the OVA-II peptide in PBS, with and without an adjuvant, at two sites in the back skin. The adjuvant used was 10 µg/mouse of the Ac vaccine adsorbed to aluminum phosphate, or $2 \times 10^7$ cells/mouse of the We vaccine. One week after the third once-a-week immunization, the mice were killed, and splenocytes were stimulated with the OVA-II peptide. Briefly, $2 \times 10^6$ DO11.10 splenocytes/well were stimulated with a series of dilutions of OVA-II in 10% FCS containing DMEM (200 µl/well). The cytokines secreted in the supernatant during incubation at 37° C. for 48 hours were quantified using Fluorokine kits for IFN-γ, IL-4, and IL-5. Cytokine concentrations were corrected by the number of $KJ1.26^+$, $CD4^+T$ cells (cells retaining DO11.10 transgenic TCR (Haskins, K. et al., (1983), J. Exp. Med. 157: 1149-1169)) present in the assay.

Tumor Inoculation Experiment 3,000,000 EL4 cells and 4,000,000 EG7 cells were intradermally inoculated to each B6 mouse on mutually opposite sides of the shaven back. Mutually perpendicular longest dimensions were measured every two days starting on day 7 after the inoculation. The number of tumor cells was determined in advance, and about the same tumor growth rate was given for the two cell lines. A group of 5 mice was immunized three times by once-a-week intradermal injection of 50 nmoles of OVA-I dissolved in PBS, with or without an adjuvant (5 µg of the Ac vaccine adsorbed to aluminum phosphate or $1 \times 10^7$ cells of inactivated pertussis whole cell body). A back skin apart from the tumor inoculation sites was used for immunization. One week after the 3rd immunization, the tumor cells were inoculated. Once-a-week immunization was further performed twice, starting 1 week after the tumor inoculation. To examine the effect of immunization with the WT1 peptide, FBL3 erythroleukemia cells were used in a tumor challenge experiment (Udaka, K. et al., (2000), J Immunol 164: 1873-1880). The mice were immunized once weekly, with or without an adjuvant, by intradermal injection of 100 nmoles of the Db126 peptide (RMFPNAPYL (SEQ ID NO:2), (Udaka, K. et al., (2000), J Immunol 164: 1873-1880)). One week after the 3rd immunization, 5,000,000 FBL3 cells were intraperitoneally injected, and the number of survival days was examined. Once-a-week peptide immunization was restarted one week after the tumor inoculation.

Long Term Immunization with the Wc Vaccine and Db126 Peptide

Each B6 mouse was intradermally immunized once weekly with $1 \times 10^9$ cells of inactivated pertussis whole cell body (100 times the amount used in the CTL induction and tumor inoculation experiment), with or without 50 nmoles of the Db126 peptide. One week after the 9th immunization, urine was collected, the mouse was killed, and blood and tissues (lung, kidney, ovary, testis, bone marrow) were collected. The tissues were fixed in 10% formalin, and paraffin sections thereof were stained with Haematoxylin & Eosin. Blood collected from the axillary aorta and vena cava was immediately diluted 10 fold in a PBS containing 10 mM EDTA, and after appropriate dilution, red blood cells (RBCs) were counted using a blood cell counting chamber. Leukocytes, after fold dilution in Turk solution to lyse RBCs, were counted in the same manner. Urinary total protein content was measured using the Micro-TP Test kit (Wako Pure Chemical Industries, Osaka).

(Results)

Adjuvant Activities of the Pertussis Vaccines

To examine the adjuvant activities of the pertussis vaccines, a model antigen system incorporating ovalbumin (OVA) as an endogenous tumor antigen was utilized (Moore, M. W. et al., (1988), Cell 54: 777-785, Hogquist, K. A. et al., (1994), Cell 76: 17-27). The $K^b$-bound OVA-I (SIINFEKL (SEQ ID NO:1)) peptide is known to be a major CTL epitope in $H-2^b$ mice (Moore, M. W. et al., (1988), Cell 54: 777-785). First, a test was performed to determine whether or not the CTL induction by OVA-I peptide immunization could be enhanced by the addition of a pertussis vaccine. First, before the CTL induction experiment, the helper inducing activities of the pertussis vaccines were tested. The helper activities were examined by testing for the production of an IgG antibody against a mixture of PT and FHA, hence mainly for Th2-biased activity. As shown in FIG. 1, the IgG antibody was very well produced within 3 weeks after immunization with the Ac vaccine. The Wc vaccine also induced production of the IgG antibody, but the amount produced was smaller than that obtained with the use of the Ac vaccine. Hence, it was shown that both the Ac vaccine and the Wc vaccine were capable of stimulating Th cell activity.

Figure 2:
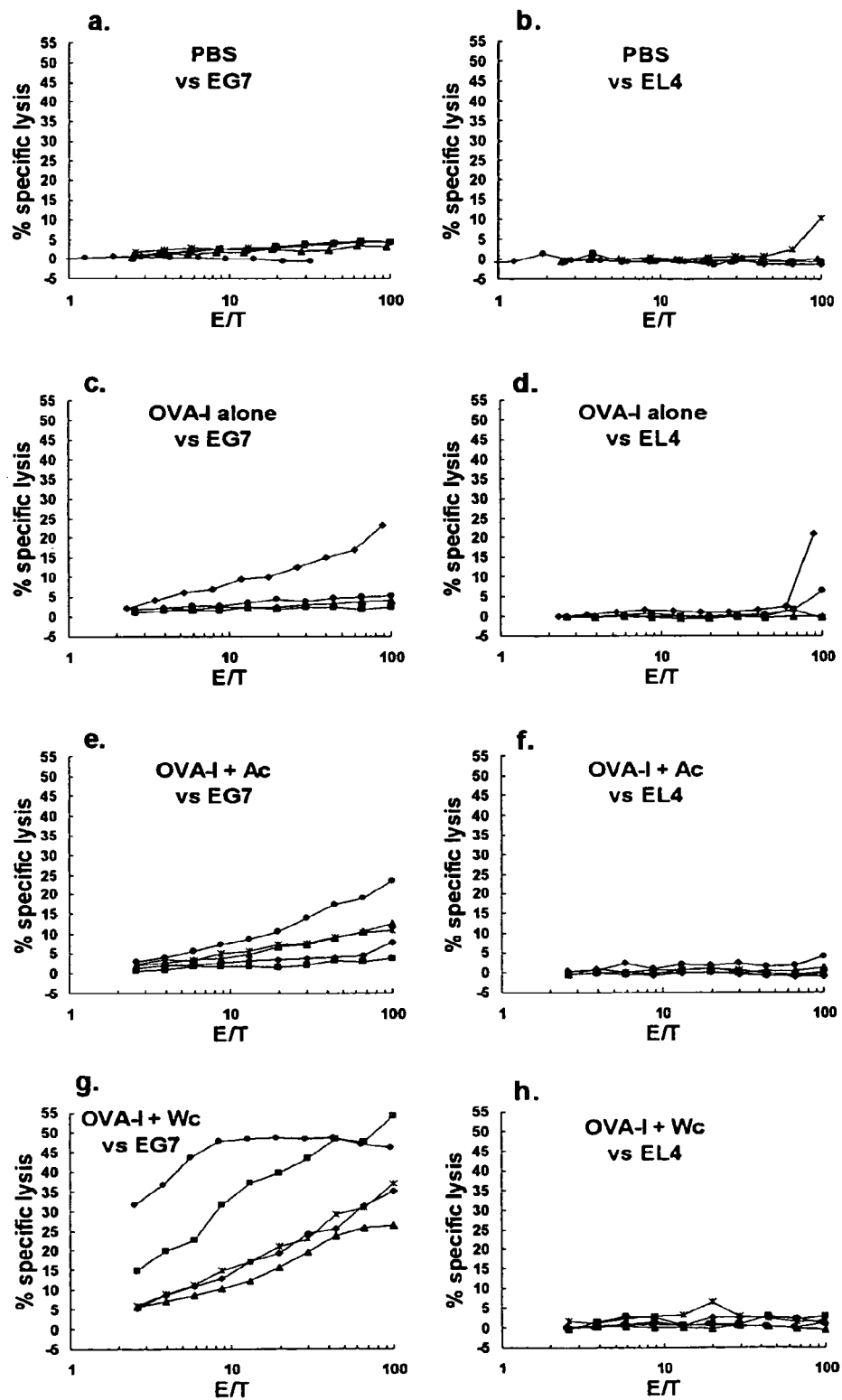
FIG. 2 Graphic representations of the induction of cytotoxic activity compared among different immunization groups. B6 mice were immunized with the OVA-I peptide, with or without a pertussis vaccine, once weekly. One week after the 4th immunization, splenocytes were examined for cytotoxic activity against EG7 (a, c, e, g), ovalbumin-transduced cells or the parent cell line EL4 (b, d, f, h). Specific lysis during incubation for 5 hours at various E/T ratios is shown. Data on splenocytes collected from individual mice are shown by respective broken lines.

Next, together with the Ac vaccine or Wc vaccine, C57BL/6 (B6) mice were immunized with the OVA-I peptide. Results of a cytotoxicity test with splenocytes immunized 4 times by intradermal injection of the peptide, with or without pertussis vaccine, used as the effector, are shown in FIG. 2. The OVA-transfected cell E.G7-OVA (EG7) (Moore, M. W. et al., (1988), Cell 54: 777-785) and the parent cell line EL4 thereof were used as the targets. When the OVA-I peptide, which is expected to lack helper activity, was administered alone, only low cytotoxic activity was induced. Occasionally, OVA-specific lysis was observed (one of the five mice in FIG. 2c, 10-20% on average for repeated experiments). This recalls patients who enjoy an anti-tumor effect in response to treatment, found accidentally in clinical studies. Several to 10% on average of the cancer-bearing patients receiving the WT1 peptide (a peptide different from the one in the present filing) alone or in emulsion in Freund's incomplete adjuvant (FIA) exhibited clinical responses demonstrating tumor suppression (Oka, Y. et al., (2004), Proc. Natl. Acad. Sci. USA 101: 13885-13890, Rosenberg, S. et al., (1998), Nat. Med. 4: 321-327). These accidental respondents are possibly those who had an environment that promoted inflammation at the immunization site under the influence of past infections and the like, and experienced stimulation of CTL thereof accidentally. When the Ac vaccine, which promotes Th2 responses, was added, the cytotoxic activity increased. Meanwhile, the Wc vaccine induced very potent cytotoxic activity in all mice. The remarkable induction of the CTL activity was observed with the Wc vaccine at high reproducibility. The responses of the Wc-immunized mice were antigen-specific, and no cytotoxicity to EL4 was observed. Thus, it was found that the potent cytotoxic activity was not due to non-specific cytotoxic activity like that of LAK cells, which are induced by a large amount of cytokines. In the splenocytes of mice immunized with Ac and Wc, particularly in cell lines with high cytotoxic activity against EG7, the ratio of CD8 T cells (CTLs) tended to rise (data not shown). Hence, next, the degree of proliferation of antigen-specific CD8 T cells in mouse bodies was examined.

In Vivo Proliferation of Antigen-Specific CD8 T Cells

Figure 3:
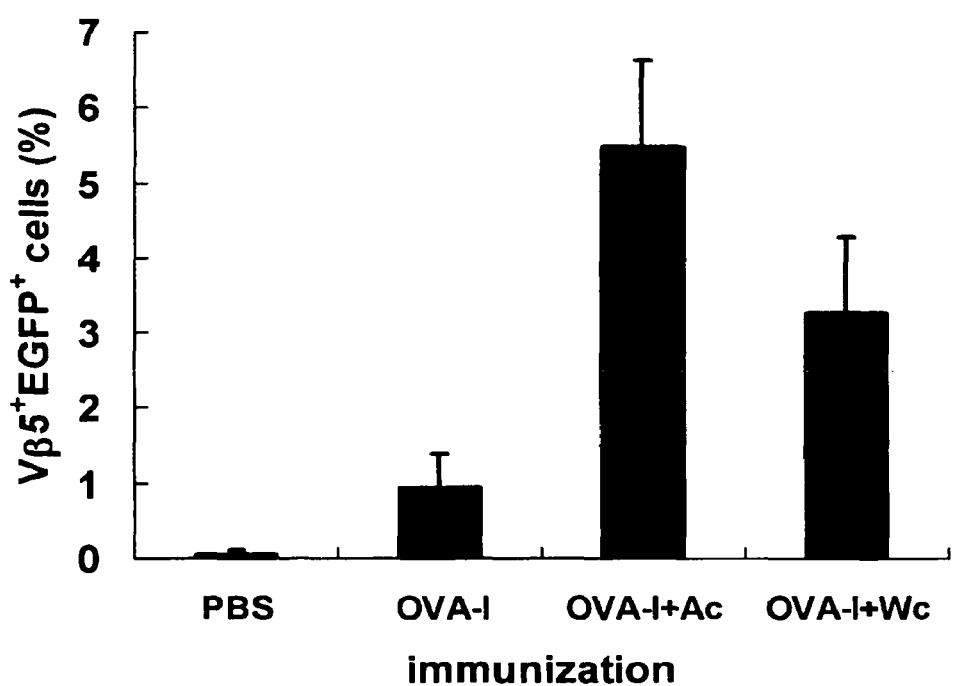
FIG. 3 A graphic representation of in vivo proliferation of EGFP$^+$OT1 cells. EGFP$^+$ OT1 cells were intravenously injected. The following day, the mice were intradermally injected with the OVA-I peptide, with or without a pertussis vaccine. In the following week, immunization was repeated in the same manner. One week after the 2nd immunization, splenocytes were examined by flow cytometry. Here is shown the ratio of cells having fluorescent transgenic TCR in the splenocytes.

To monitor the in vivo proliferation of tumor antigen-specific T cells, splenocytes of an OVA-I-specific TCR transgenic mouse (011) mated with a transgenic mouse that expresses EGFP under the control of a chicken β-actin promoter and cytomegalovirus enhancer were adoptively transferred into a normal mouse. In these EGFP transgenic mice, not all T cells express EGFP, although the reason remains unclear (Okabe, M. et al., (1997), FEBS Letters 407: 313-319). Of the CD8 T cells in the spleen, 80±10 (SD) % were positive for EGFP expression. A monoclonal anti-$V_\beta 5$-specific antibody, MR9-4 (Kanagawa, O. et al., (1991), J. Immunol. 147: 1307-1314), was used to identify transgenic TCRs. As shown in FIG. 3, OT1-TCR$^+$, EGFP$^+$CD8 T cells had decreased nearly to the limit of detection in the spleen by 15 days after intravenous injection. However, when the mice were intradermally immunized twice with the OVA-I peptide alone, transgenic OT1-TCR$^+$, EGFP$^+$, CD8 T cells proliferated to an observable level. When a pertussis vaccine was added to the OVA-I peptide, OT1 cells exhibited further proliferation. Interestingly, the proliferation of OT1 cells with the Ac vaccine was found to be slightly stronger than by Wc with high reproducibility. Judging from this result, Ac possessed an activity to increase the number of antigen-specific T cells, but, as seen in FIG. 2, the cytotoxic activity was not so potent. In contrast, the Wc vaccine was highly effective in inducing potent cytotoxic activity. To produce cytotoxic activity, it is necessary for the cells to undertake a new protein synthesis to produce perforin and granzymes, which are components of cytotoxic granules. The immunity-stimulating environment induced by the Wc vaccine might play a role in this induction of protein synthesis.

Th1/Th2 Cytokine Profile of CD4 T Cells Stimulated with Pertussis Vaccine

Figure 4:
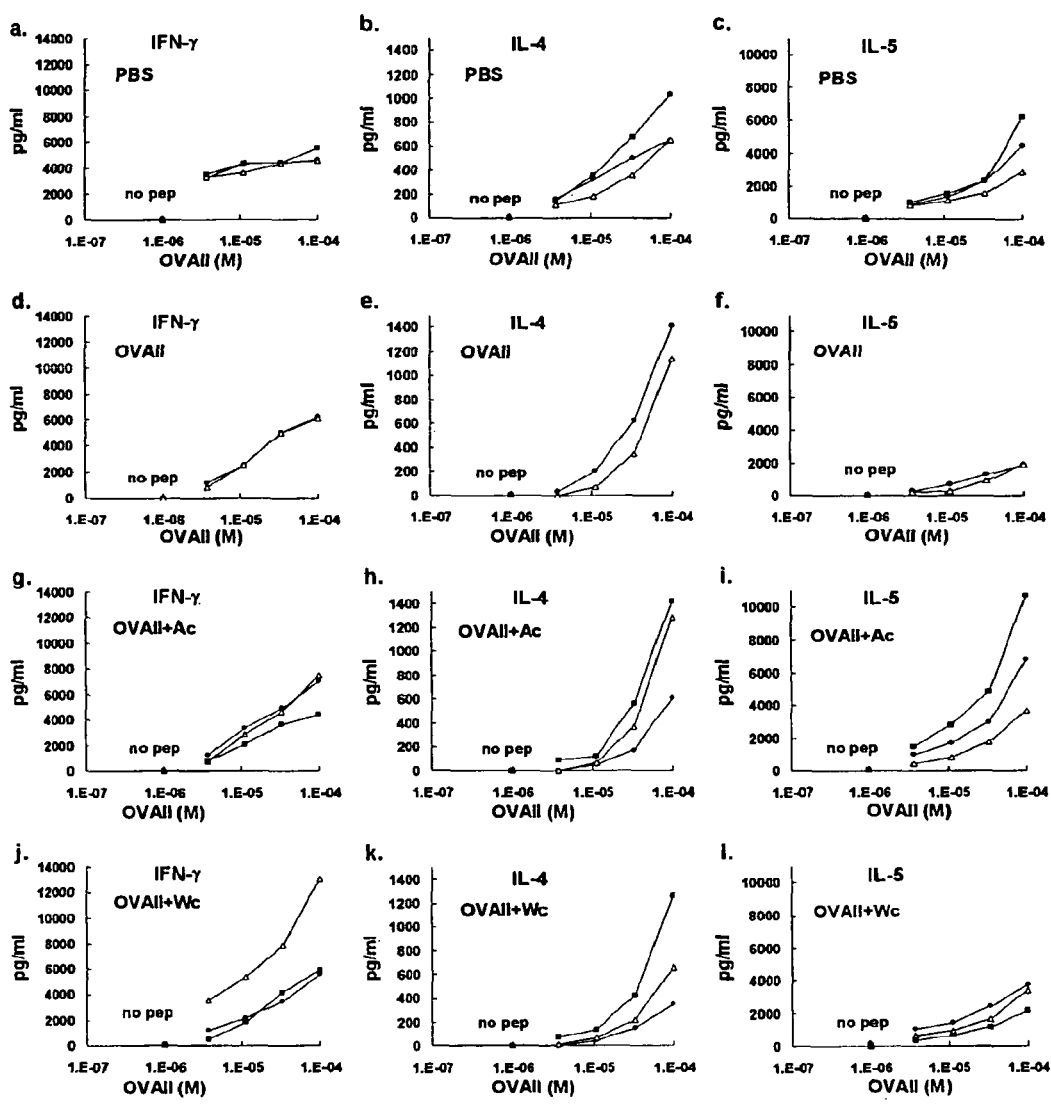
FIG. 4 Graphic representations of Th1/Th2 cytokine production in DO11.10 mice immunized with the OVA-II peptide, with or without a pertussis vaccine. One week after the 3rd once-a-week immunization, splenocytes were collected, stimulated with the OVA-II peptide, and examined for cytokine production. The cytokines IFN-γ, IL-4 and IL-5 were measured using the Luminex 100 and Fluorokine MAP kit. Here are shown cytokine concentrations in culture supernatants after 48 hours of incubation following the antigen stimulation. The Ac vaccine induced the production of larger amounts of type Th2 cytokines (IL-4 and IL-5), whereas the We vaccine promoted the production of larger amounts of type Th1 cytokine (IFN-γ) and tended to produce smaller amounts of the Th2 cytokines.

Next, an attempt was made to determine whether or not the pertussis vaccine added as the adjuvant influenced the profile of cytokines secreted by T cells stimulated with a heterogeneous peptide antigen unrelated to *B. Pertussis*, the T cells being present in the vicinity. For a model antigen system, DO11.10 TCR transgenic (DO11.10tg) CD4 T cells were used as the responder. DO11.10 TCR is specific for the OVA-II peptide bound to the I-A$^d$ molecule (323-339, ISQAVHAAHAEINEAGR (SEQ ID NO:3), (Hunt, D. F. et al, (1992), Science 256: 1817-1820)). A DO11.10tg mouse intradermally immunized with the OVA-II peptide dissolved in PBS, with or without a pertussis vaccine, as described in the Materials and Methods. One week after three once-a-week immunization, the spleen was collected and stimulated with the OVA-II peptide. After 48 hours, the culture supernatant was recovered, and the cytokine content was measured. As shown in FIG. 4, DO11.10 T cells, which were identified for the first time by IL-2-producing activity (Haskins, K. et al., (1983), J. Exp. Med. 157: 1149-1169), produced a considerable amount of interferon-γ (IFN-γ) (FIG. 4a). When the mouse was immunized with the We vaccine, higher production of IFN-γ, a type Th1 cytokine, was observed with high reproducibility. In contrast, peptide immunization with the Ac vaccine induced higher production of IL-5, a type Th2 cytokine. Production of IL-4, another type Th2 cytokine, did not differ so much among different immunization groups. However, when administered alone or together with the OVA-II peptide, the AC vaccine tended to induce higher IL-4 production. These results suggest that the inflammatory environment induced by a pertussis vaccine may also influence T cells specific for unrelated antigens, the T cells being present in the vicinity.

Considering the risk of inducing self-attacking responses as a result of active stimulation of Th cells to tumor antigens (mostly self-proteins), it seems to be a safer strategy to stimulate stationary CTLs with foreign-antigen-specific Th cells. Immune responses to foreign antigens escape self-tolerance and are generally more potent. Furthermore, if immune responses are in excess, and in the case of a foreign antigen, antigen supply can easily be stopped by stopping immunization.

In Vivo Tumor Rejection Reactions

Figure 5:
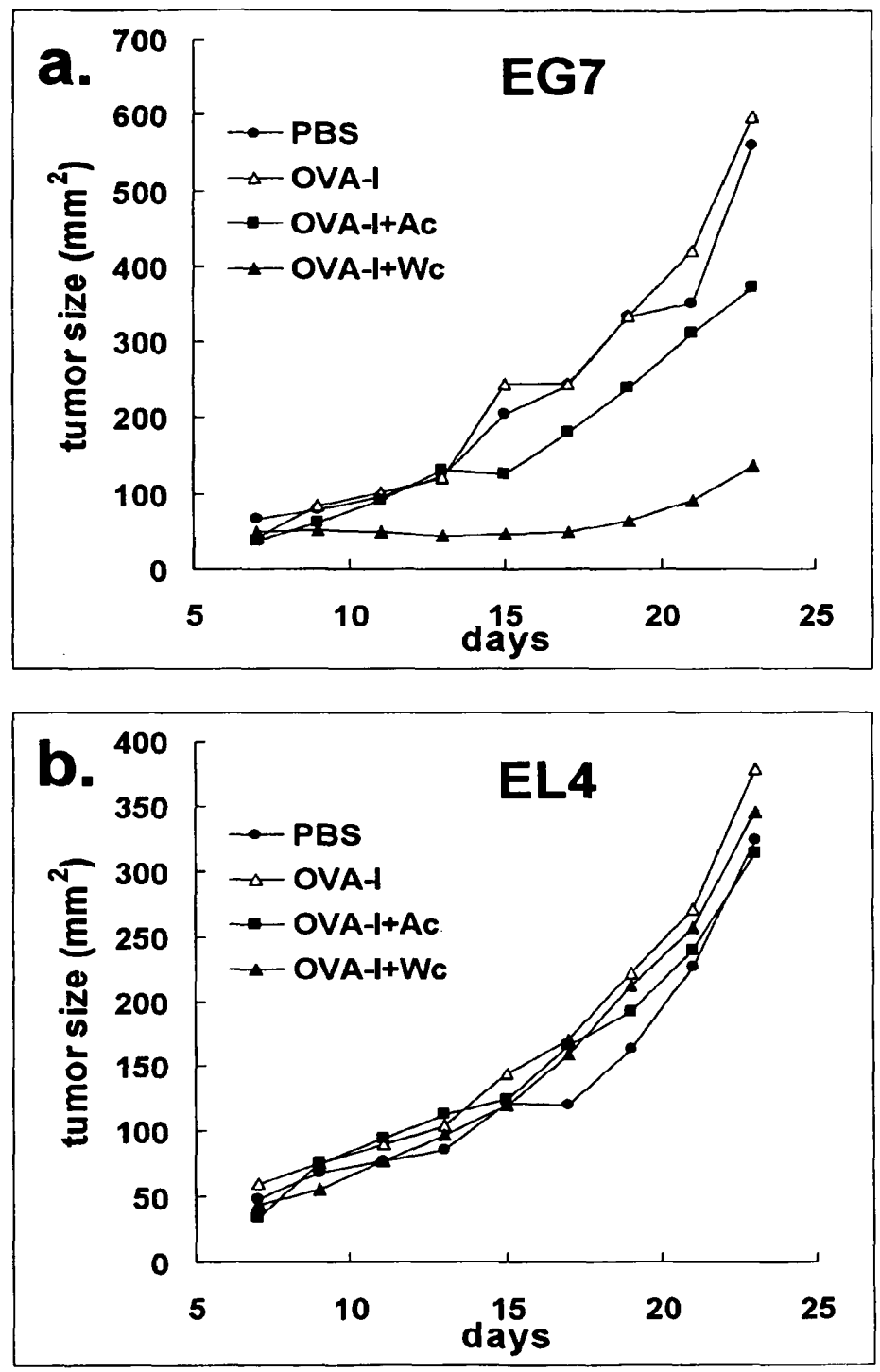
FIG. 5 Graphic representations of in vivo tumor proliferation in mice immunized with the OVA-I peptide, with or without a pertussis vaccine. After the 3rd once-a-week immunization, EG7 and EL4 cells were intradermally inoculated to B6 mice on mutually opposite sides of their backs. Tumor size, as the product of major diameter and minor diameter perpendicular thereto, was measured every two days. The data are shown as mean for five mice.

Next, it was determined whether or not peptide immunization with a pertussis vaccine promoted tumor rejection in vivo. After the OVA-I peptide was injected, with or without a pertussis vaccine, mice were intradermally inoculated with EG7 and parent EL4 tumor cells once weekly 3 times. One week after the inoculation, once-a-week peptide immunization was restarted. As shown in FIG. 5, immunization with the peptide alone had no significant effect on tumor proliferation. This recalls the low clinical responses observed when cancer-bearing patients were immunized with the peptide alone or together with an adjuvant having almost no adjuvant activity, like FIA, in clinical studies (Rosenberg, S. A. et al., (2004), Nat. Med. 10: 909-915, Oka, Y. et al., (2004), Proc. Natl. Acad. Sci. USA 101: 13885-13890, Nencioni, A. et al., (2004), Ann. Oncol. 15: 153-160, Romero, P. et al., (2004), Cancer Immunol. Immunother. 53: 249-255). When the Ac vaccine was added as an adjuvant, the tumor proliferation became slower to some extent. In contrast, the Wc vaccine potently suppressed tumor proliferation. Unlike other Th1 inducing adjuvants such as tubercle *bacillus* components, the Wc vaccine did not produce open ulcers even when administered in repeated immunization. This is a further advantage of the Wc vaccine when brought into clinical application.

In Vivo Induction of Anti-Tumor Responses to WT1 Tumor Autoantigen

Figure 6:
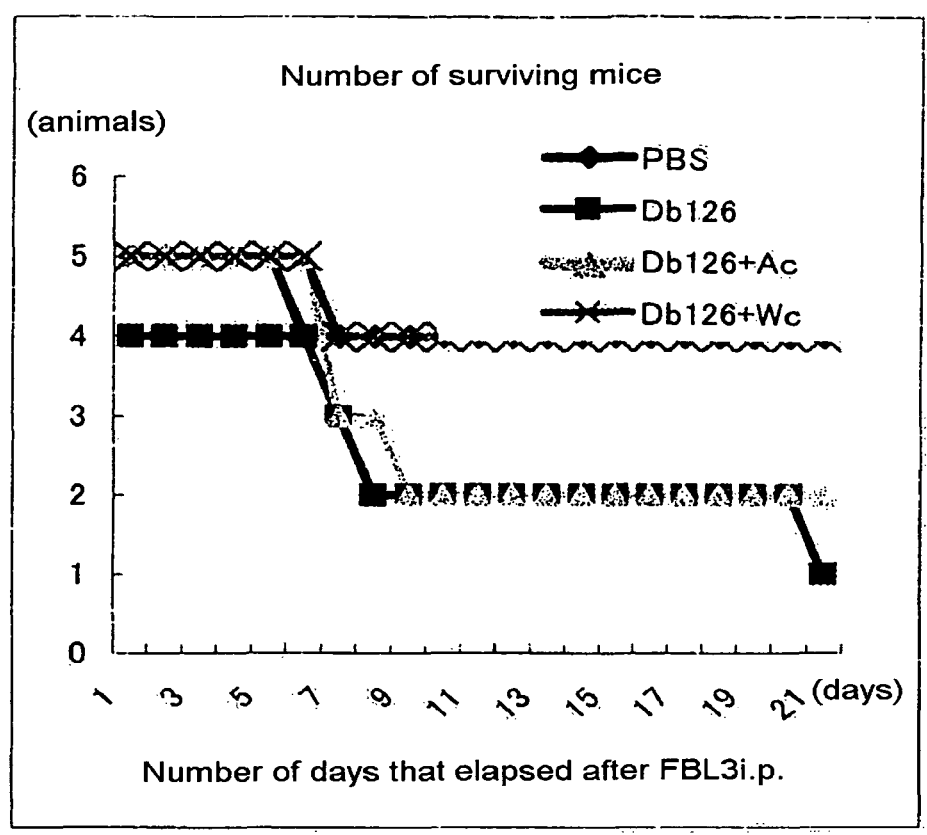
FIG. 6 A graphic representation of the effect of immunization on mouse survival examined with intraperitoneal injection of a lethal dose of FBL3 tumor cells. Each group of five B6 mice were immunized 3 times in advance by once-a-week intradermal administration of the Db126 WT1 peptide, with or without a pertussis vaccine. FBL3 cells were then intraperitoneally injected, and the survival of the mice was monitored. The data shown are representative ones from reproducible experiments.

In the above-described experiment, foreign antigen OVA was used as a model tumor antigen enabling easier elicitation of immune responses. Next, it was determined whether or not a pertussis vaccine helped induce anti-tumor responses to a tumor autoantigen. For this purpose, as the tumor antigen, a Wilms' tumor 1 (WT1) gene product (Udaka, K. et al., (2000), J Immunol 164: 1873-1880) was targeted. The present inventors previously identified the epitope Db126 (126-134, RMFPNAPYL (SEQ ID NO:2)) derived from a mouse WT1 product that was presented by the D$^b$ molecule and induced anti-tumor CTL responses. FBL3 erythroleukemia cells were used as a tumor that spontaneously expresses a high level of the WT1 product. Since the FBL3 cells did not proliferate sufficiently when injected intradermally, the survival of mice given a lethal dose of intraperitoneally injected FBL3 cells was monitored. As shown in FIG. 6, immunization with the peptide alone induced very weak anti-tumor activity. When the Ac vaccine was administered, the number of mice that died decreased. In contrast, all of the mice immunized with the Wc vaccine and peptide survived. As a result, it was shown that in the tumor rejection experiment wherein the self-tumor peptide was targeted, the Wc vaccine exhibited potent adjuvant activity.

Figure 7:
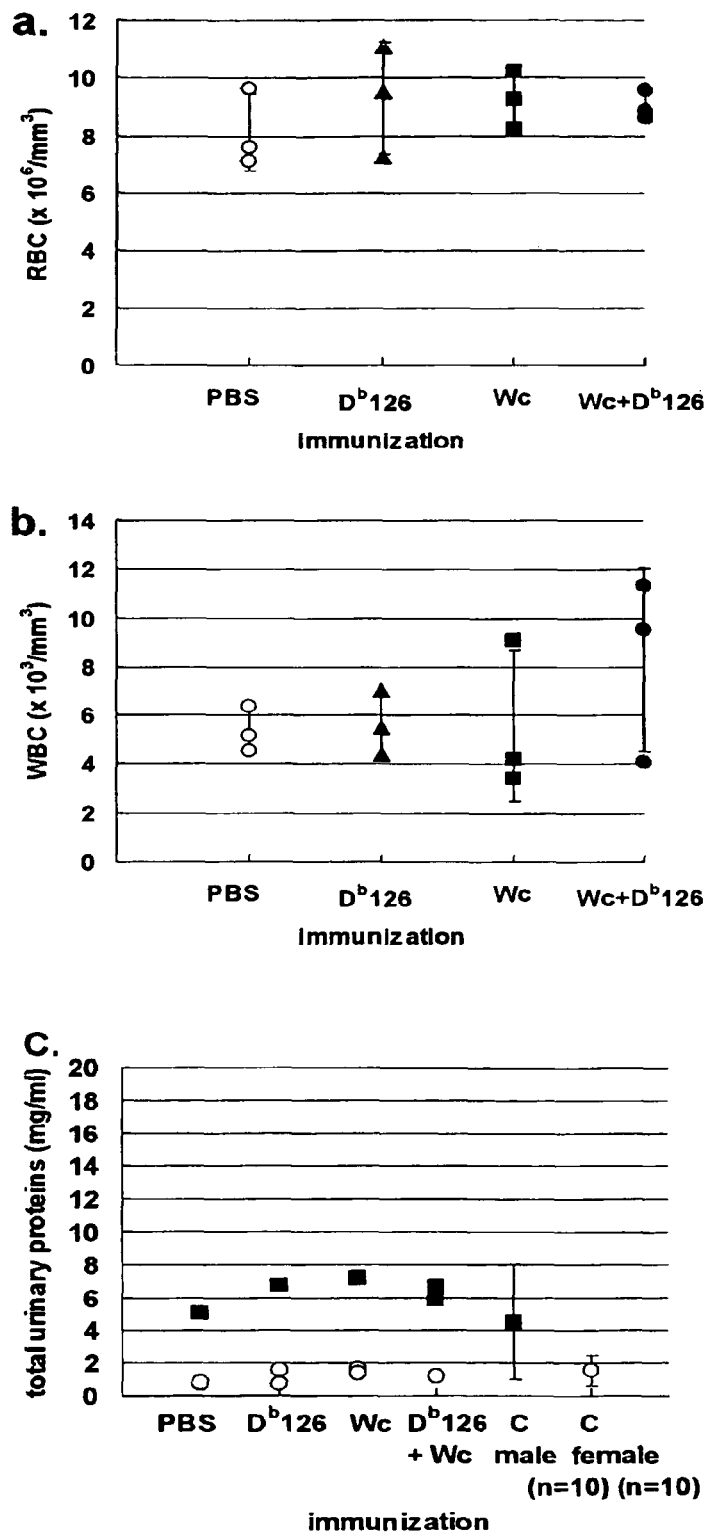
FIG. 7 Graphic representations of urinary and hematological findings in long immunized mice. Urinary total protein volume and blood erythrocyte (a.) and leukocyte counts (b.) were determined in the long immunized mice shown in FIG. 8. Each error bar indicates a mean and standard deviation. For urinary protein, the mean and standard deviation for 10 normal B6 mice of each sex are shown for control.

Long Term Effects of Repeated Immunization with Tumor Peptide and Pertussis Vaccine The adjuvant activity of the Wc vaccine proved to be very potent; as a result, it was suggested that the Wc vaccine might induce aggressive responses to self-proteins to cause adverse reactions. For human application in the future, this will be a key point. Hence, with the addition of the Wc vaccine, immunization with the WT1 peptide was repeated for a long time, and reactions were examined. WT1 tumor antigen is expressed, although in small amounts, even in normal tissues, specifically in hematopoietic stem cells in the bone marrow, the pleura and peritoneum, which are of mesothelial origin, renal podocytes, testis, ovary and, probably various stem cells. The Db126 WT1 peptide alone or Wc alone, or a mixture of Db126 and Wc, was repeatedly administered once a week in a total of eight immunizations, and adverse reactions were checked for. The amount of the Wc vaccine used for the immunization was 100 times larger than the amount that had been used previously ($1\times10^9$ inactivated bacterial cells). One week after the final immunization, urinary protein and peripheral blood cell counts, as well as tissues were examined. As a result, in any immunization group, no abnormalities were observed in any tissue examined. No abnormalities were observed in urinary protein or hematology (FIG. 7).

Figure 8:
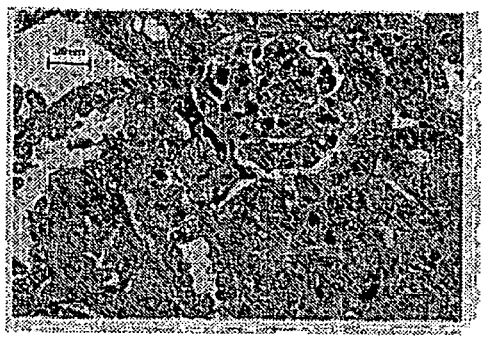
FIG. 8 Plates showing tissues of mice after long-term immunization with the Wc vaccine and the Db126 WT1 peptide. Here are shown kidneys (a.c.) and lungs (b.d.) from mice immunized with PBS (a.c.) and the Wc vaccine and the Db126 peptide (b.d.) once weekly 8 times. Paraffin sections were stained with Hematoxylin and Eosin. There were no significant changes such as lymphocyte invasion.
Figure 8:
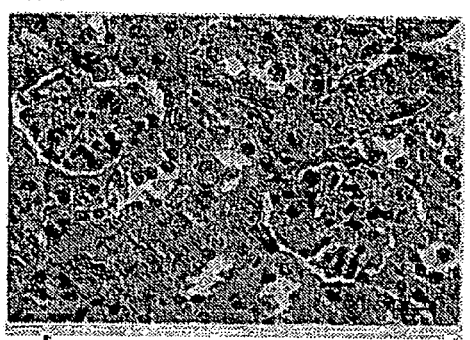
Figure 8:
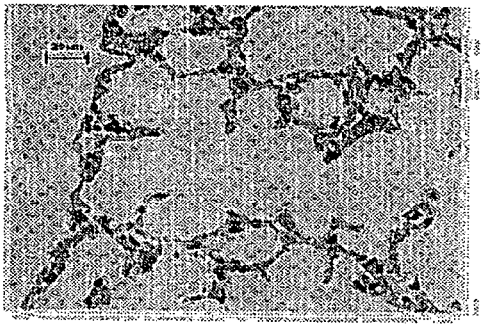
Figure 8:
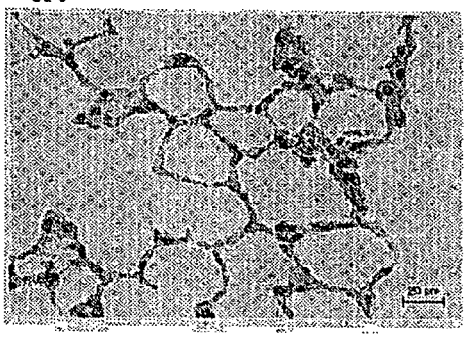

Kidneys and lungs of mice immunized with the Db126 peptide and Wc vaccine once weekly 9 times are shown in FIG. 8. In any immunization group, there were no signs of autoimmune responses such as lymphocyte invasion or tissue damage. From these results, it was found that even when a peptide immunotherapy targeting a WT1 tumor antigen, a self-protein, was repeated for a long time, adverse self-attacking reactions did not occur.

Clinical Studies of Malignant Tumors Using WT1 Tumor Antigen Peptide

At Kochi University School of Medicine Hospital, using the W10 peptide (ALLPAVPSL (SEQ ID NO:4)) as a WT1 tumor antigen peptide and the whole cell body pertussis vaccine (Wc) as an adjuvant, phase I/II clinical studies in patients with various malignant solid tumors were performed (some are ongoing). A single-dose amount of the peptide (1 or 3 mg) was dissolved in 300 µl of 5% glucose solution, and this was admixed with $5\times10^8$ Wc cells suspended in 100 µl of physiological saline just before administration, to obtain a total of 400 µl of a vaccine suspension. The vaccine suspension, 100 µl, was intradermally injected into each of the four skin sites in both axillae and both inguinal regions, using a syringe and needle for self-injection of insulin.

The dosing protocol varied depending on the patient; typically, one week after 3 administrations of W10 alone, examination for a safety test and an evaluation of therapeutic effect were performed, a data management committee was held to determine the acceptability of continued treatment, and the patients for whom the treatment was determined to be continued, the regimen was shifted to W10+Wc administration at an interval of 1 or 2 weeks. The specific dosing protocols for the individual cases are as follows.

Test Number KB07-001:
W10 (3 mg) administered alone 5 times→a 2-week interval→W10 1 mg+$5\times10^8$ Wc administered 3 times→followed by W10 3 mg+$5\times10^8$ Wc administration which is ongoing Test Number KB07-002:
W10 1 mg+$5\times10^8$ Wc administered twice→followed by W10 3 mg+$5\times10^8$ Wc administration which is ongoing Test Number KB07-003:
W10 (3 mg) alone administered 4 times→a 2-week interval, W10 1 mg+$5\times10^8$ Wc administered 3 times→followed by W10 3 mg+$5\times10^8$ Wc administration which is ongoing Test Number KB07-005:
W10 (1 mg) administered alone 3 times→subsequently, W10 (3 mg) administered alone 5 times→a 2-week interval, W10 1 mg+$5\times10^8$ Wc administered 3 times→followed by W10 3 mg+$5\times10^8$ Wc administration which is ongoing Test Number KB07-006:
W10 (1 mg) administered alone 3 times→subsequently, W10 (3 mg) administered alone 4 times→a 2-week interval, W10 1 mg+$5\times10^8$ Wc administered 3 times→followed by W10 3 mg+$5\times10^8$ Wc administration which is ongoing Test Number KB07-007:
From the beginning, W10 3 mg+$5\times10^8$ Wc administered 10 times. After 7 weeks, the rating was determined to be PD. After 10 times of administration, the rating turned to PS3 and the test treatment was completed.

Test Number KB07-009:
From the beginning, W10 3 mg+$5\times10^8$ Wc administered 6 times. The tumor necrotized and dropped, infection occurred from the wound, the general condition worsened, and the treatment was discontinued.

Test Number KB07-011:
W10 (3 mg) administered alone 5 times→a 4-week interval, W10 1 mg+$5\times10^8$ Wc administered once→followed by W10 3 mg+$5\times10^8$ Wc administration continued, the treatment was completed with the rating of PD after the 21st.

Test Numbers KB07-012 and KB07-013:
From the beginning, W10 3 mg+$5\times10^8$ Wc administered, and this is ongoing.

Test Number KB07-017:
From the beginning, W10 3 mg+$5\times10^8$ Wc administered 6 times. Diagnostic imaging (PET-CT) at the 6th week determined the rating to be PD. The treatment was completed.

Safety was evaluated using CTCAE (Common Terminology Criteria for Adverse Events v3.0) by JCOG/JSCO-Oct. 27, 2004 as rating criteria for adverse events; if the rating was grade 2, the treatment was broken, if the rating was grade 3 or more, irrespective of causal relation with the test treatment, the treatment was discontinued.

Figure 9:
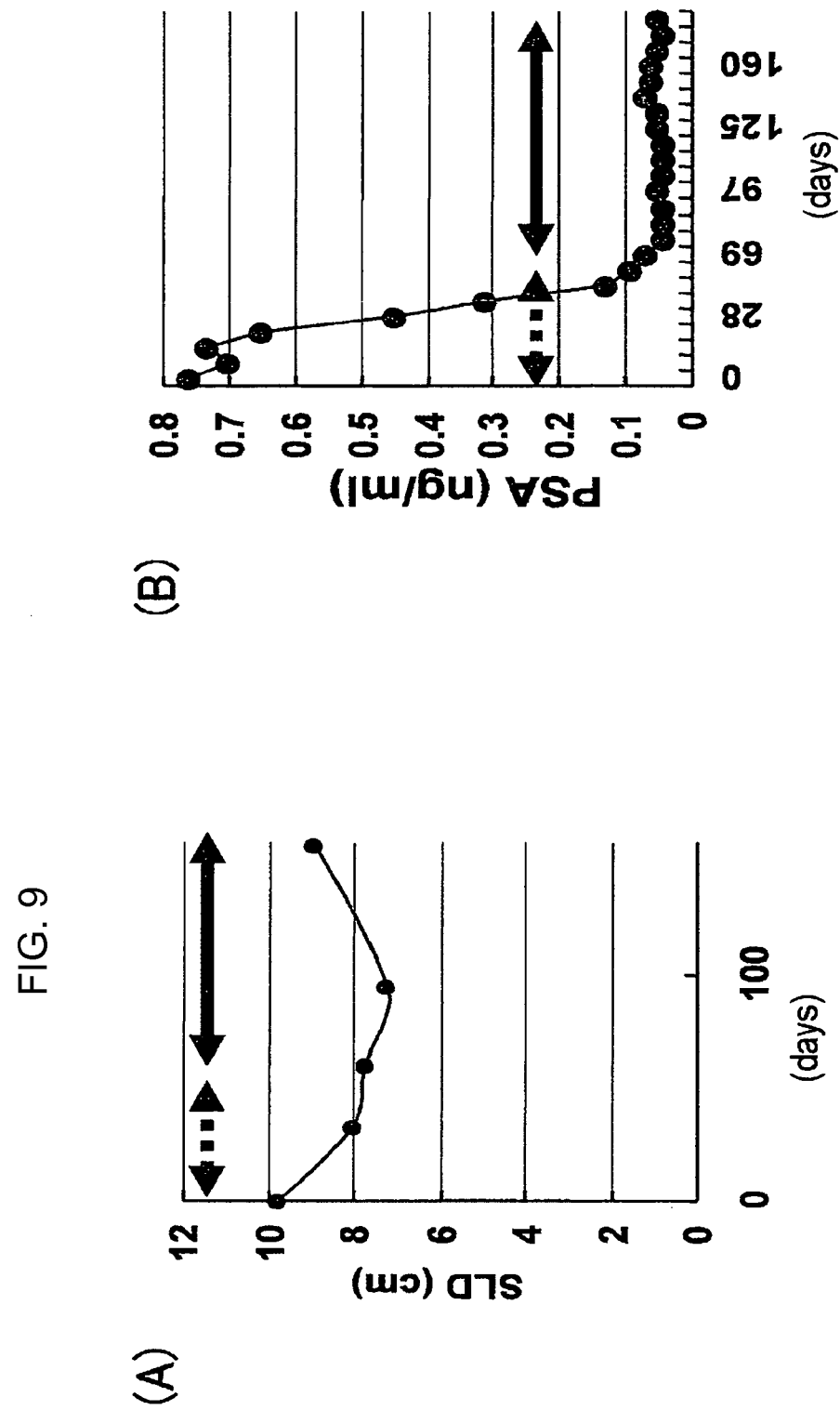
FIG. 9 Graphic representations of results of early phase I/II clinical studies of an immunotherapy using the W10 peptide in a prostatic cancer patient KB07-005 with a right femoral bone metastasis. (A) shows changes in sum longest diameter (SLD) of tumor over time after the start of treatment. The dotted arrow indicates the duration of administration of W10 alone; the solid arrow indicates the duration of co-administration of W10 and a whole cell pertussis vaccine (Wc). The change in SLD at 14 weeks after addition of Wc was 115%, the RECIST rating being SD. (B) shows changes in PSA concentration over time after the start of treatment. The dotted arrow indicates the duration of administration of W10 alone; the solid arrow indicates the duration of co-administration of W10 and the whole cell pertussis vaccine (Wc).
Figure 10:
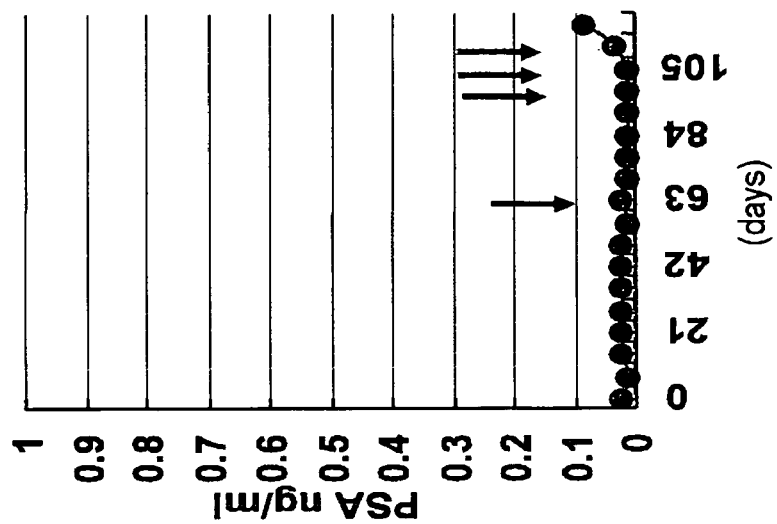
FIG. 10 Graphic representations of results of early phase I/II clinical studies of an immunotherapy using the W10 peptide in a prostatic cancer patient KB07-003 with pubic metastasis who had undergone radiotherapy for target bone lesions. (A) shows changes in sum of the longest diameters (SLD) of tumor over time after the start of treatment. The dotted arrow indicates the duration of administration of W10 alone; the right solid arrow indicates the duration of co-administration of W10 and a whole cell pertussis vaccine (Wc). The left solid arrow indicates the duration of radiotherapy. The change in SLD at 14 weeks after addition of Wc was 58%, the RECIST rating being PR. (B) shows changes in PSA concentration (originally a PSA-positive tumor) over time after the start of treatment. Each arrow indicates a washout made because of Cre elevation.
Figure 10:
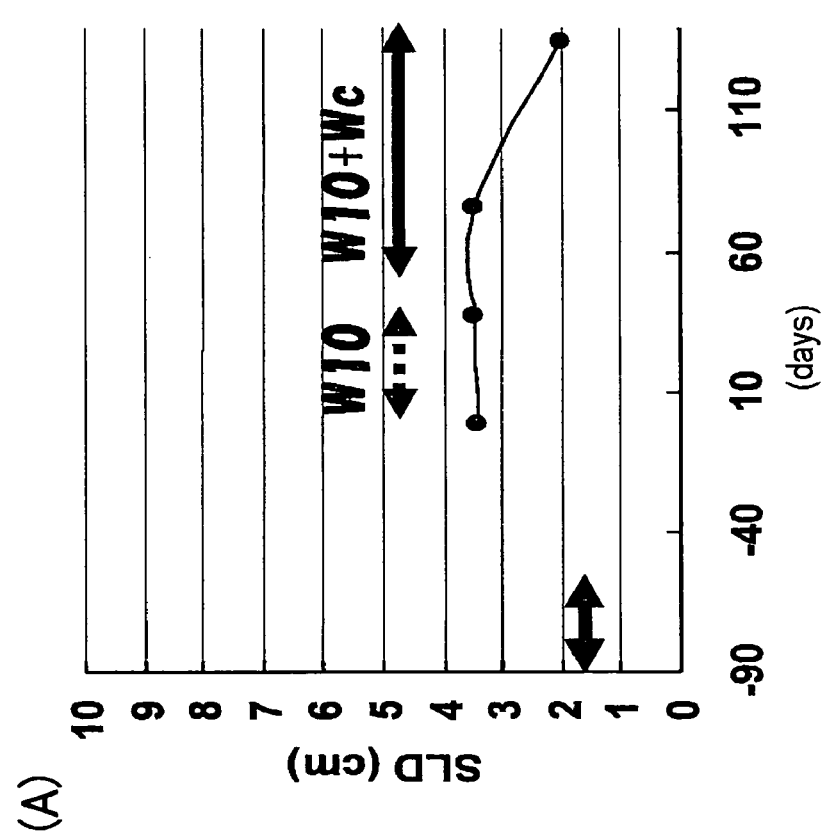
Figure 11:
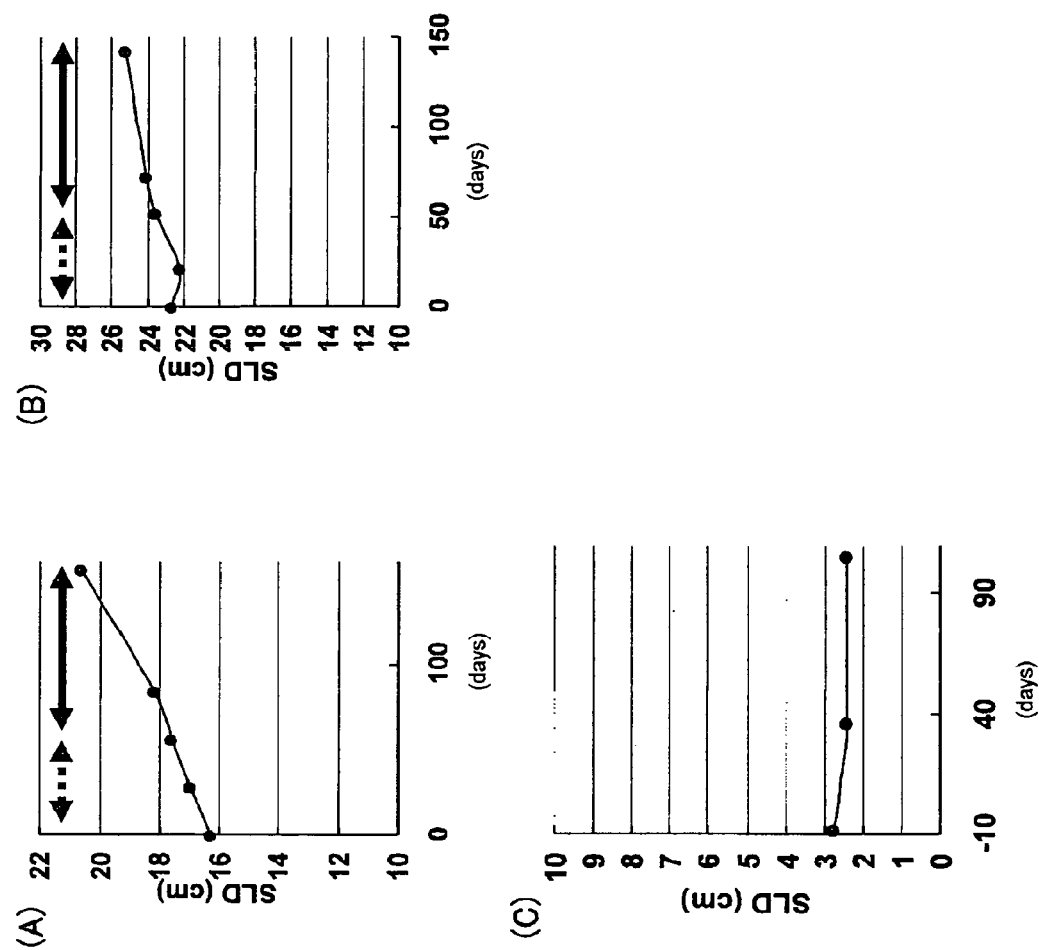
FIG. 11 Graphic representations of results of early phase I/II clinical studies of an immunotherapy using the W10 peptide in (A) an oral adenoid cystic carcinoma patient KB07-006, (B) a bronchial adenoid cystic carcinoma patient KB07-001 with multiple pulmonary metastases, and (C) an extramammary Paget's disease patient KB07-002. Each axis of ordinates indicates sum of the longest diameters (SLD) of tumor; each axis of abscissas indicates the number of days after the start of treatment. Each dotted arrow indicates the duration of administration of W10 alone; each right solid arrow indicates the duration of co-administration of W10 and a whole cell pertussis vaccine (Wc). For (C), W10 and the whole cell pertussis vaccine (Wc) were concomitantly administered from the beginning. (A) At 14 weeks after addition of Wc, the SLD change was 117%, the RECIST rating being SD. (B) At 14 weeks after addition of Wc, the SLD change was 107%, the RECIST rating being SD. (C) At 13 weeks after addition of Wc, the SLD change was 87%, the RECIST rating being SD.

Treatment efficacy was evaluated according to the RECIST Criteria (Theresse, P. et al., J Natl Cancer Inst. 2000, 92, 205-216). Specifically, as determined by helical CT or MRI, if all target lesions disappeared, the rating was CR (complete response); if the sum longest diameter of target lesions decreased by 30% or more, the rating was PR (partial response); if the sum longest diameter of target lesions increased by 20% or more, the rating was PD (progressive disease); if the finding did not meet the criteria for PR or PD, the rating was SD (stable disease). If even one new lesion emerged, irrespective of the presence or absence of a target lesion, the rating was determined to be PD. The results are shown in Table 1 and FIGS. 9 to 11.

TABLE 1

| | | | | | | | | |
|---|---|---|---|---|---|---|---|---|
| | | | | Patients treated for solid malignant tumors | | | | |
| Test No. | sex | Disease(s) | Starting day | 3 administrations completed | Continued treatment | Number of administrations | Course | RECIST rating |
| KB07-001 | M | Bronchial adenoid cystic carcinoma, multiple pulmonary metastases | 2007 Oct. 4 | ○ | ○ | 18 | Administered 18 times until January 31. After 14 weeks, CT determined the rating to be SD. | SD |

TABLE 1-continued

Patients treated for solid malignant tumors

| Test No. | sex | Disease(s) | Starting day | 3 administrations completed | Continued treatment | Number of administrations | Course | RECIST rating |
|---|---|---|---|---|---|---|---|---|
| KB07-002 | F | Extramammary Paget's disease | 2007 Oct. 9 | ○ | ○ | 17 | Administered 17 times until January 29. After 14 weeks, CT determined the rating to be SD. | SD |
| KB07-003 | M | Prostatic cancer, pubic metastasis | 2007 Oct. 4 | ○ | ○ | 13 | PSA fell gradually until 15th week. Although MRI determined the rating to be SD (images are presented for reference purposes since radiotherapy was performed 3.5 months before the start of treatment), a washout was made because of an elevation of Cre. After the washout, PSA rose again (0.01→0.03). | SD(due to PSA) |
| KB07-005 | M | Prostatic cancer, right femoral bone metastasis | 2007 Oct. 3 | ○ | ○ | 18 | Tumor marker decreased gradually until 17th week. After 14 weeks, MRI determined the rating to be SD. | SD |
| KB07-006 | F | Oral adenoid cystic carcinoma | 2007 Oct. 4 | ○ | ○ | 18 | Administered 18 times until January 31. After 14 weeks, CT determined the rating to be SD. | SD |
| KB07-007 | M | Pulmonary large-cell carcinoma, multiple intrapulmonary metastases, multiple pelvic bone | 2007 Nov. 12 | ○ | ○ | 10 | After 7 weeks, the rating was PD. In particular, the pelvic bone metastases expanded diffusely. Thereafter, pleural fluid exacerbated, the rating turned to PS3, and the test treatment was ended. | PD |
| KB07-009 | F | Maxillary gingival cancer | 2007 Nov. 1 | ○ | ○ | 6 | Localized DTH was observed, primary focus rupture and infection occurred, and the patient was hospitalized. The patient became unable to eat, and the test treatment was ended. | Not evaluable |
| KB07-0011 | M | Desmoplastic small round cell tumor | 2007 Oct. 16 | ○ | ○ | 14 | After 4 weeks, CT determined the rating to be SD; however, after 12 weeks, CT revealed remarkable progression of hepatic metastasis. Ileus due to pelvic tumor exacerbated, and the test treatment was discontinued. | PD |
| KB07-0012 | F | Colorectal cancer | 2007 Nov. 19 | ○ | ○ | 9 | On Jan. 7, 2008, the test treatment was discontinued because of PD (persistent elevation of tumor marker). | PD |
| KB07-0013 | F | Malignant melanoma, multiple pulmonary metastases | 2007 Nov. 15 | ○ | ○ | 12 | Although the rating for underlying lesion was SD, very small lesions emerged newly. Switch to IFN-β combination therapy is being considered. | PD |
| KB07-0017 | M | Submandibular gland cancer | 2007 Dec. 21 | ○ | ○ | 6 | Test drug treatment ongoing, no evaluation performed after the start of treatment. | PD |

Of the 11 patients who completed 6 times or more of W10+Wc administration, 10 permitted an efficacy assessment by the RECIST Criteria, of whom half 5 were given the rating SD (Table 1). For KB07-003 (FIG. 10), the change in SLD after the start of addition of Wc was 58% during 14 weeks, resulting in the rating of PR according to the RECIST Criteria; however, because the patient had a history of radiotherapy for the target bone lesion, so that a possible tardive effect thereof could not be ruled out; according to the criterion "PSA level remains at the limit of measurement", the rating was determined to be SD (Table 1). For KB07-009, with a peak reached at 48 hours after administration, there were severe flare and swelling, and pain in the cancer metastasis portion, but these remitted in about 2 days, and this was repeated even after the next peptide immunization. After the start of peptide immunotherapy, imaging revealed a dramatic change, in which the tumor mass involving the inside of the temporal bone and oral cavity to the neck skin lysed rapidly, but a hole formed penetrating from the oral cavity to the neck skin, infection from the wound occurred, and the general condition worsened, so that the treatment was discontinued, and RECIST evaluation could not be made (Table 1).

Taking into consideration the fact that little studies have been reported wherein the ratio of SD or higher exceeded 10% (in another test using a WT1 antigen peptide and FIA as an adjuvant, SD was obtained in less than 20% of the patients who completed 12 times of once-a-week administration and permitted a RECIST evaluation; data not shown), and that most of the patients being the subjects of treatment in this test were patients with advanced cancers having multiple metastases who did not respond to any other treatment, the results of this test clearly demonstrate the efficacy of the therapeutic method of the present invention.

INDUSTRIAL APPLICABILITY

Because pertussis vaccines exhibit excellent adjuvant activity in the administration of cancer antigen peptides and virus antigen peptides, and have been safely used as vaccines as they are, the agents of the present invention, which comprise such a vaccine as an adjuvant, are useful in the treatment of cancers and viral infectious diseases.

This application is based on patent application No. 2007-028081 filed in Japan (filing date: Feb. 7, 2007), and the contents disclosed therein are hereby entirely incorporated by reference. In addition, the contents disclosed in any publication cited herein, including patents and patent applications, are hereby incorporated in their entireties by reference, to the extent that they have been disclosed herein.

The invention claimed is:

1. A therapeutic agent for malignant tumor or a prophylactic agent for malignant tumor metastasis or recurrence, comprising a MHC class I binding peptide comprising a portion of the amino acid sequence WT1, and a pertussis vaccine, and a carrier, the pertussis vaccine is a whole cell pertussis vaccine, and the whole cell pertussis vaccine is an adjuvant,
wherein the peptide is present in an amount of 0.1 to 5 mg and the vaccine is present in an amount of $1 \times 10^8$ to $1 \times 10^9$ cells of the whole cell pertussis vaccine.

* * * * *